(12) United States Patent
Ayala et al.

(10) Patent No.: US 10,107,686 B1
(45) Date of Patent: Oct. 23, 2018

(54) VISION STRIP ANALYZER

(71) Applicant: Ayalytical Instruments, Inc., Chicago, IL (US)

(72) Inventors: Juan Ayala, Chicago, IL (US); Eric W Larson, Chicago, IL (US); Darren Bolgioni, Cary, IL (US)

(73) Assignee: AYALYTICAL INSTRUMENTS, INC., Chicago, IL (US)

( * ) Notice: Subject to any disclaimer, the term of this patent is extended or adjusted under 35 U.S.C. 154(b) by 368 days.

(21) Appl. No.: 14/637,162

(22) Filed: Mar. 3, 2015

Related U.S. Application Data

(60) Provisional application No. 61/947,407, filed on Mar. 3, 2014.

(51) Int. Cl.
*G01J 3/46* (2006.01)
*G01J 3/50* (2006.01)
*G01J 3/02* (2006.01)

(52) U.S. Cl.
CPC ............. *G01J 3/463* (2013.01); *G01J 3/0202* (2013.01); *G01J 3/0275* (2013.01); *G01J 3/50* (2013.01)

(58) Field of Classification Search
CPC ...... G01J 3/46; G01J 3/463; G01J 3/50; G01J 3/52
See application file for complete search history.

(56) References Cited

U.S. PATENT DOCUMENTS

| | | | | |
|---|---|---|---|---|
| 2,566,079 A | * | 8/1951 | Bruning | G01J 3/52 356/420 |
| 3,712,466 A | * | 1/1973 | Aubry | G01N 21/952 209/538 |
| 3,916,168 A | * | 10/1975 | McCarty | G01J 3/0251 356/405 |
| 4,874,940 A | * | 10/1989 | McMeekin | G01N 21/9018 250/223 B |
| 4,999,511 A | * | 3/1991 | Kohno | G01N 21/94 250/559.11 |
| 5,206,918 A | * | 4/1993 | Levene | G01J 3/46 382/110 |
| 5,751,847 A | * | 5/1998 | Wuyts | G01J 3/46 382/165 |
| 5,919,707 A | | 7/1999 | Banks et al. | |
| 6,598,464 B1 | | 7/2003 | Rossi | |
| 6,901,163 B1 | * | 5/2005 | Pearce | B07C 5/36 382/165 |
| 7,589,539 B2 | | 9/2009 | Butler et al. | |
| 8,614,739 B2 | | 12/2013 | Pollack et al. | |

(Continued)

FOREIGN PATENT DOCUMENTS

| | | | | |
|---|---|---|---|---|
| GB | 2489253 A | * | 9/2012 | ......... G01N 21/8851 |
| JP | 58091655 A | | 5/1983 | |

OTHER PUBLICATIONS

Andersen, Wendy C., Aziz I. Abdulagatov, and Thomas J. Bruno. "The ASTM copper strip corrosion test: Application to propane with carbonyl sulfide and hydrogen sulfide." Energy & fuels 17.1 (2003): 120-126.*

Primary Examiner — Tri Ton
Assistant Examiner — Rufus Phillips
(74) *Attorney, Agent, or Firm* — Rathe Lindenbaum LLP

(57) ABSTRACT

An apparatus includes an image system for obtaining a digital image of a test strip and a processing system to identify the colors of the test strip, compare the colors to a standard and identify the likelihood that the test strip falls with the standard.

13 Claims, 9 Drawing Sheets

(56) References Cited

U.S. PATENT DOCUMENTS

| | | | |
|---|---|---|---|
| 2005/0043898 A1* | 2/2005 | Linsen | G01J 3/52 |
| | | | 702/22 |
| 2005/0174586 A1* | 8/2005 | Yoshida | G06T 11/001 |
| | | | 358/1.9 |
| 2005/0265649 A1 | 12/2005 | Silva et al. | |
| 2006/0018748 A1* | 1/2006 | Tran | G03F 7/70741 |
| | | | 414/758 |
| 2008/0265146 A1 | 10/2008 | Coates | |
| 2012/0288195 A1* | 11/2012 | Lings | G01J 3/0264 |
| | | | 382/167 |
| 2013/0307865 A1* | 11/2013 | Manabe | G01J 3/463 |
| | | | 345/594 |

\* cited by examiner

FIG. 1

- TEST METHOD: ASTM D130
- SAMPLE ID: 77777
- OPERATOR: OPERATOR 2
- DESCRIPTION: THIS IS A TEST
- SIZE: PASS — WIDTH: 12.41 MM, HEIGHT: 74.79 MM
- SIDE 1: 3a — DARK TARNISH
- SIDE 2: 3a — DARK TARNISH
- OVERALL: 3a — DARK TARNISH

FIG. 1a

VIEW SIDE 1 / VIEW SIDE 2

RANK SCORES:
- 0 — FRESHLY POLISHED
- 1a — SLIGHT TARNISH
- 1b — SLIGHT TARNISH
- 2a  7%  MODDERATE TARNISH
- 2b — MODDERATE TARNISH
- 2c — MODDERATE TARNISH
- 2d — MODDERATE TARNISH
- 2e  42%  MODDERATE TARNISH
- 3a  49%  DARK TARNISH
- 3b — DARK TARNISH
- 4a — CORROSION
- 4b — CORROSION
- 4c — CORROSION

FIG. 1b

VIEW SIDE 1 / VIEW SIDE 2

RANK SCORES:
- 0 — FRESHLY POLISHED
- 1a — SLIGHT TARNISH
- 1b — SLIGHT TARNISH
- 2a — MODDERATE TARNISH
- 2b  6%  MODDERATE TARNISH
- 2c — MODDERATE TARNISH
- 2d — MODDERATE TARNISH
- 2e  41%  MODDERATE TARNISH
- 3a  52%  DARK TARNISH
- 3b — DARK TARNISH
- 4a — CORROSION
- 4b — CORROSION
- 4c — CORROSION

ASTM COPPER STRIP CORROSION STANDARDS
ASTM METHOD D 130 / IP 154

| FRESHLY POLISHED | 1a | 1b | 2a | 2b | 2c | 2d | 2e | 3a | 3b | 4a | 4b | 4c |
|---|---|---|---|---|---|---|---|---|---|---|---|---|
| | SLIGHT TARNISH | | MODDERATE TARNISH | | | | | DARK TARNISH | | CORROSION | | |

FIG. 2

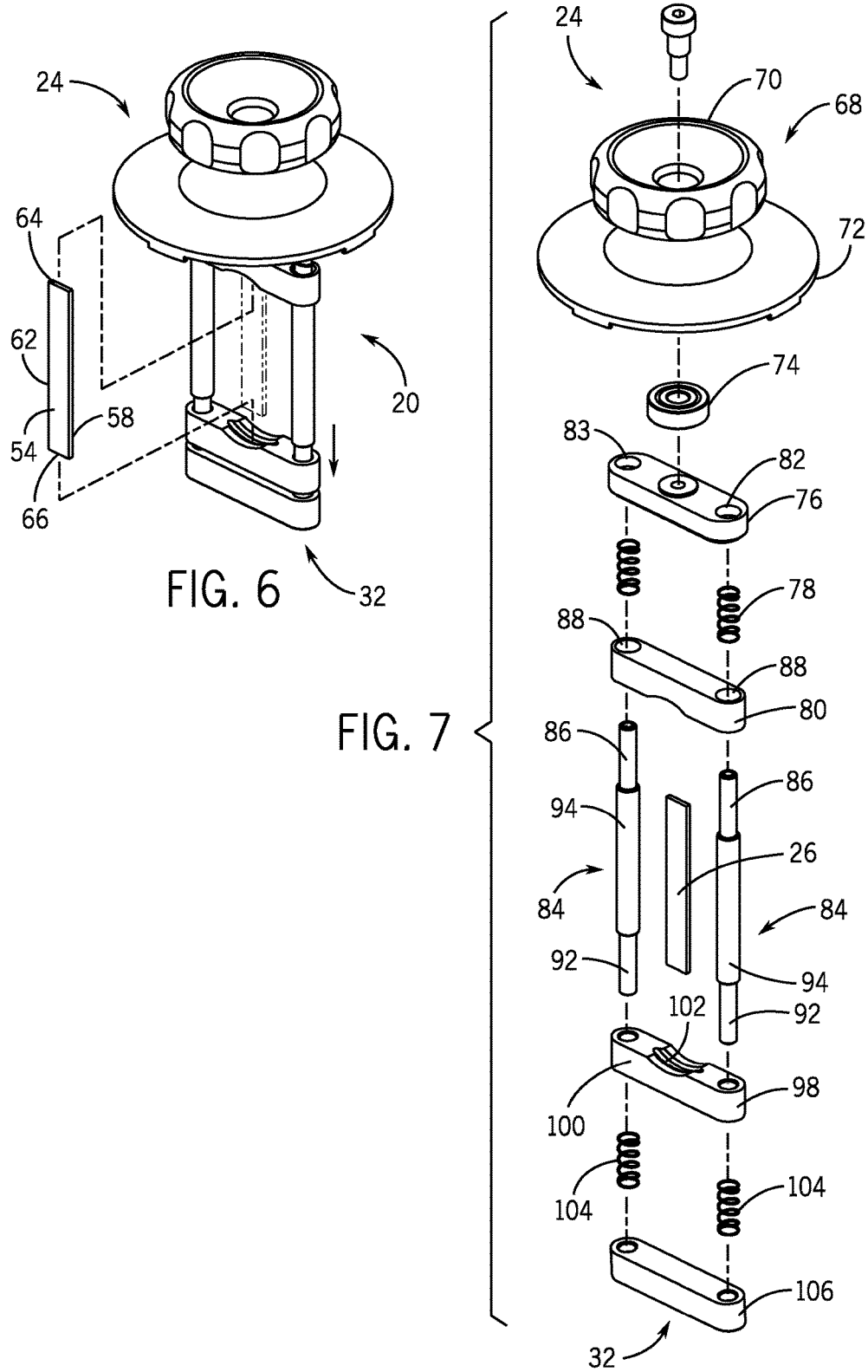

VISION STRIP ANALYZER

CROSS REFERENCE TO RELATED APPLICATIONS

This application claims priority to U.S. Patent Application No. 61/947,407 entitled Vision Strip Analyzer filed on Mar. 3, 2014 and is incorporated herein by reference in its entirety.

BACKGROUND OF THE INVENTION

The American Society for Testing and Materials (ASTM) has developed a standard test to determine whether compounds in a petroleum product have a corroding action on various metals. In one standard a copper strip is exposed to a petroleum product of interest. The copper strip after being exposed to the petroleum product is compared to color change of the copper strip provides information as to the corrosive nature of the petroleum compound. In one ASTM standard a user visually compares the treated copper strip to an ASTM standard color chart and selects the category most similar to the treated copper strip.

SUMMARY OF THE INVENTION

An apparatus includes an image system for obtaining a digital image of a test strip and a processing system to identify the colors of the copper test strip and compare the colors to a standard. A processing unit is configured to determine a likelihood that the colors in the test strip match a standard category.

In one embodiment an apparatus for analyzing the color of a test strip: a housing operatively supporting a vision system; a test strip holder configured to support a test strip; a drive mechanism operatively coupled to the test strip holder to rotate the test strip holder 180 degrees; and a processing unit operatively coupled to the vision system to receive digital image data of a first side of the test strip and a second side of the test strip; the processing unit including instructions to analyze the received imaging data; and compare the imaging data to a known standard.

In one embodiment a method for analyzing a test strip includes positioning a test strip within a vision chamber. A digital image of the test strip is obtained and received at a processing unit. The digital image is segmented of the test strip into a plurality of regions. The color of each region is determined and an algorithm determines the likelihood that the test strip is covered by one of a plurality of standard categories.

BRIEF DESCRIPTION OF THE DRAWINGS

This application will become more fully understood from the following detailed description, taken in conjunction with the accompanying figures, wherein like reference numerals refer to like elements in which:

FIG. 1 is an exemplary display of a vision system analyzer.

FIG. 1a is an exemplary display of the results of a first side of a test strip.

FIG. 1b is an exemplary display of the results of a second side of a test strip.

FIG. 2 is a chart from an ASTM standard.

FIG. 3 is an isometric view of a vision system with certain walls being see through.

FIG. 6 is an isometric view of the copper strip holder with the copper test strip removed from the copper strip holder.

FIG. 7 is an exploded view of the copper strip holder.

DETAILED DESCRIPTION OF THE PREFERRED EMBODIMENTS

Referring to FIG. 2 ASTM standard D130 entitled ASTM Copper Corrosion by Petroleum Products provides a test method for determining and classifying the extent to which corrosive compounds are present in petroleum products. FIG. 2 is provided as a black and white representation of the color standard and is provided for general information only and is not an actual depiction of the ASTM D130 standard which is publicly available. The method provides instructions on using a copper strips to classify the corrosive aspect of petroleum products. In one embodiment ASTM standard copper strips exposed to petroleum product pursuant to the ASTM method and are compared to a standard chart to classify the level of tarnish to the copper strip. The comparison may be done manually by an operator or lab technician by visually comparing the color of the treated test strips with the colors in the standard chart.

Figure 3:
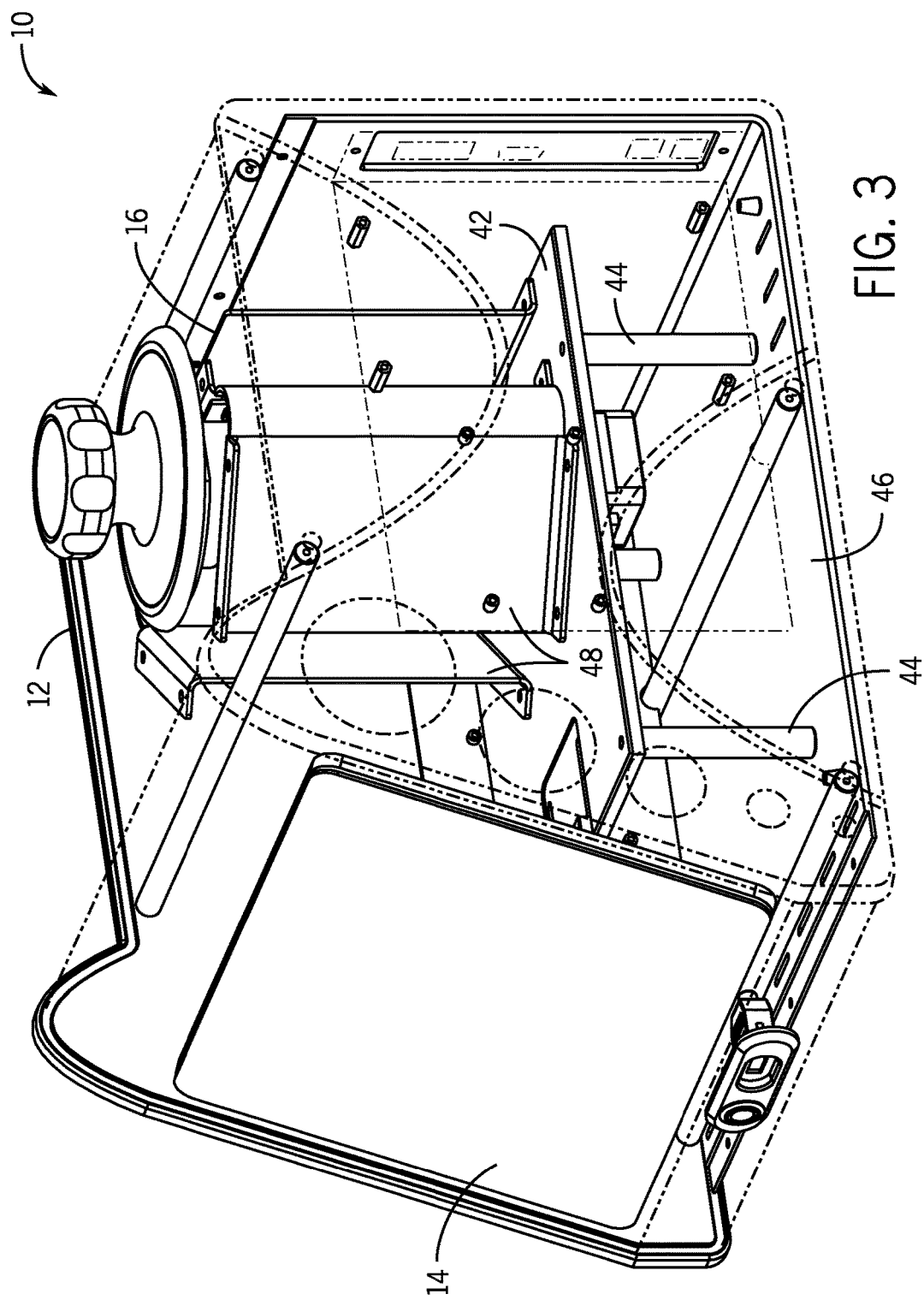

Referring to FIG. 3 in one embodiment a vision strip analyzer 10 provides an automated analysis and comparison of the test trips to a standard. Analyzer 10 includes a housing 12 supporting a display 14 which may also serve as a user input such as a touch screen. Inner analyzer chamber 16 is supported within outer housing 12.

Figure 4:
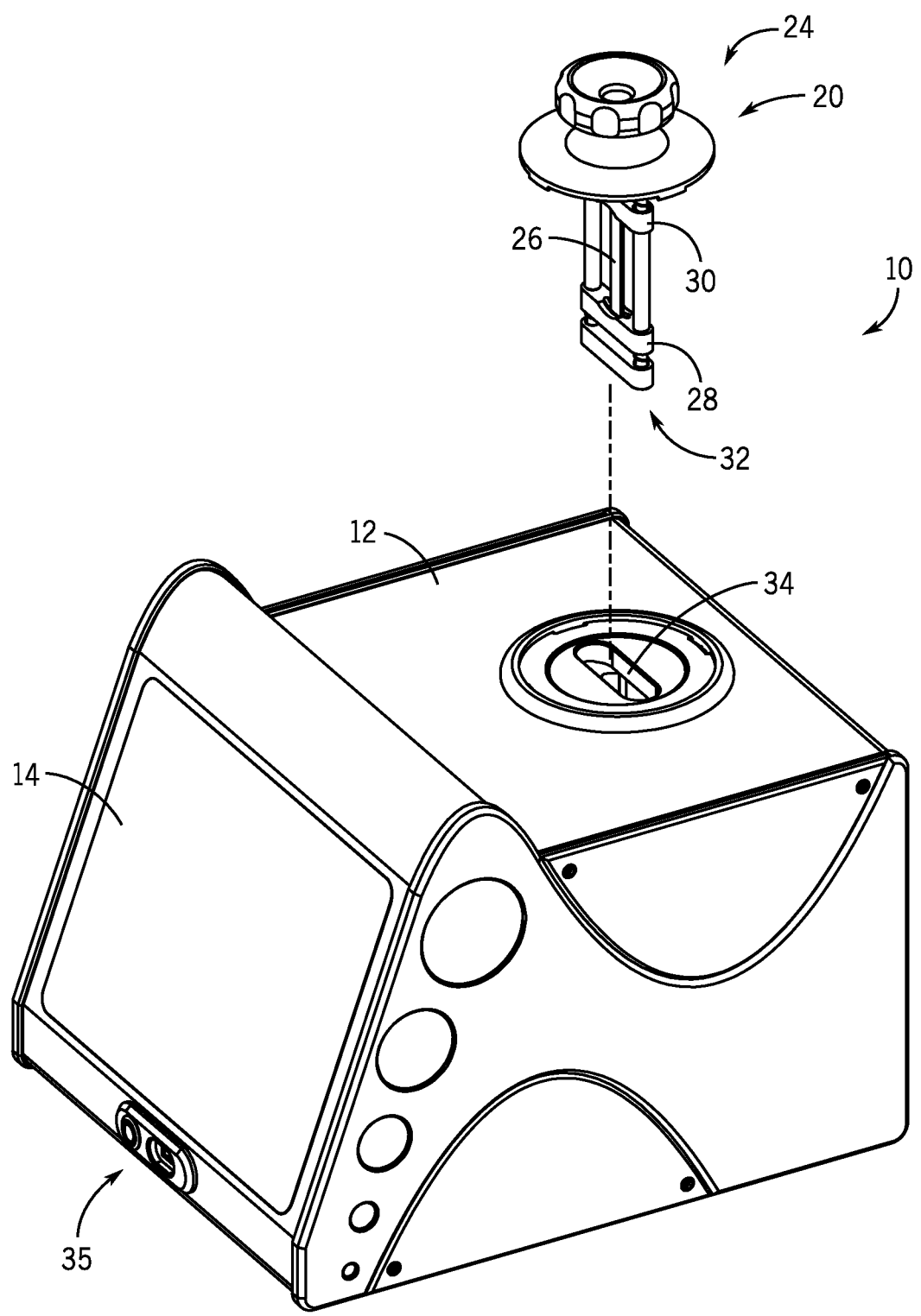
FIG. 4 is an isometric view of a copper strip holder removed from the vision system.
Figure 5:
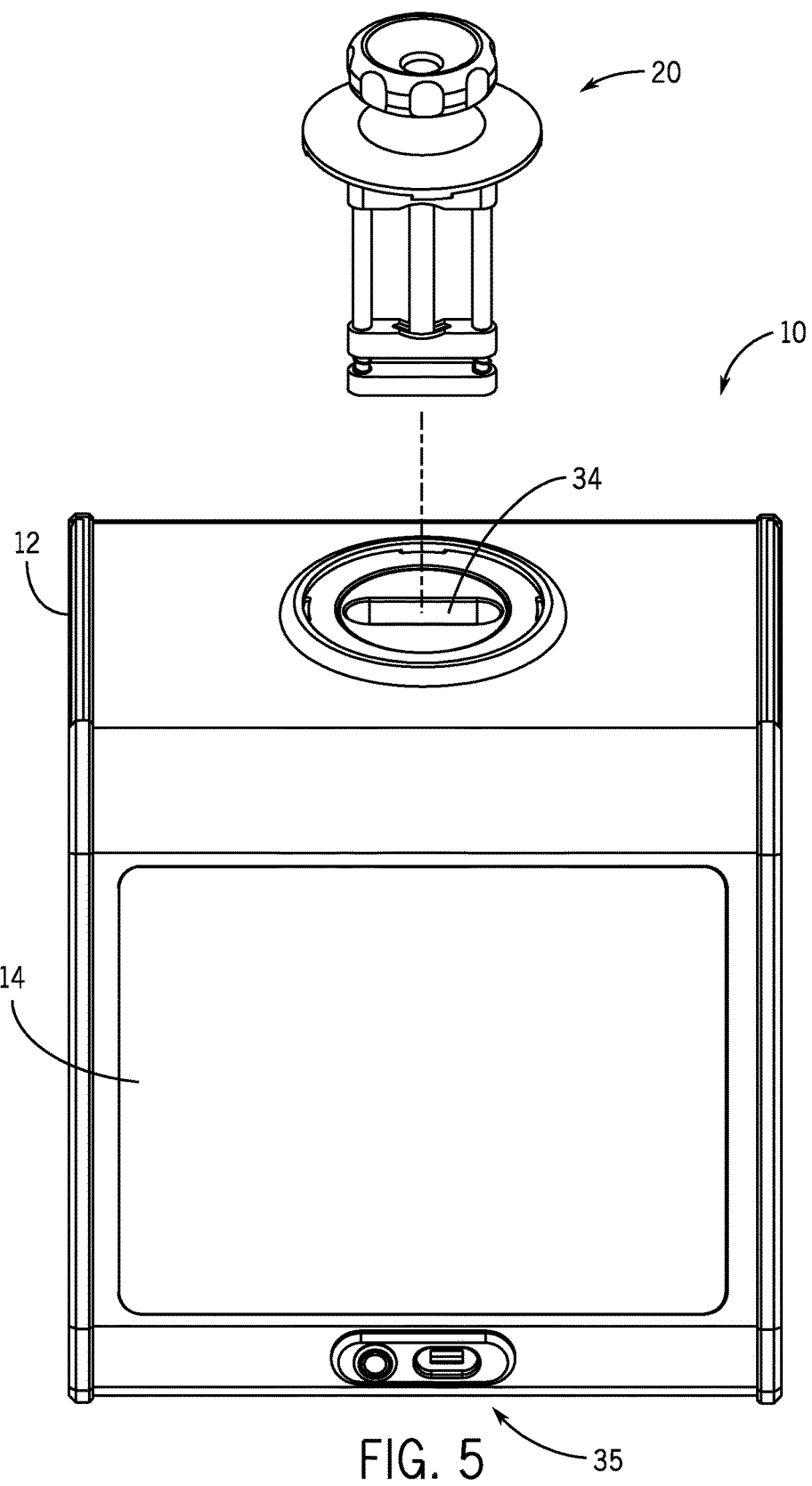
FIG. 5 is a front view of the copper strip holder removed from the vision system.

Referring to FIG. 4 a copper strip holder 20 includes a top 24 and opposing bottom 32. A test strip 26 is supported between the top 24 and bottom 32 as will be described in further detail herein. The test strip 26 is held in a self-centering manner to position test strip 26 between the top 24 and bottom 32. Self-centering members center the copper strip being analyzed between top 24 and bottom 32. Strip holder 20 may be removed from inner housing 16 through an opening or aperture 34. While ASTM standard D130 utilizes a test strip having copper material, test strip 26 may be of any other material that a standard may require.

A power and/or electronic input 35 may be provided to allow external devices such as a printer or power outlet to bet connected thereto. In one embodiment input 35 is located on a front portion of housing 12. In other embodiments input 35 may be positioned on other sides of housing 12. It is also contemplated that inputs 35 may be wireless and communication with a standard such as Bluetooth may be employed.

Figure 9:
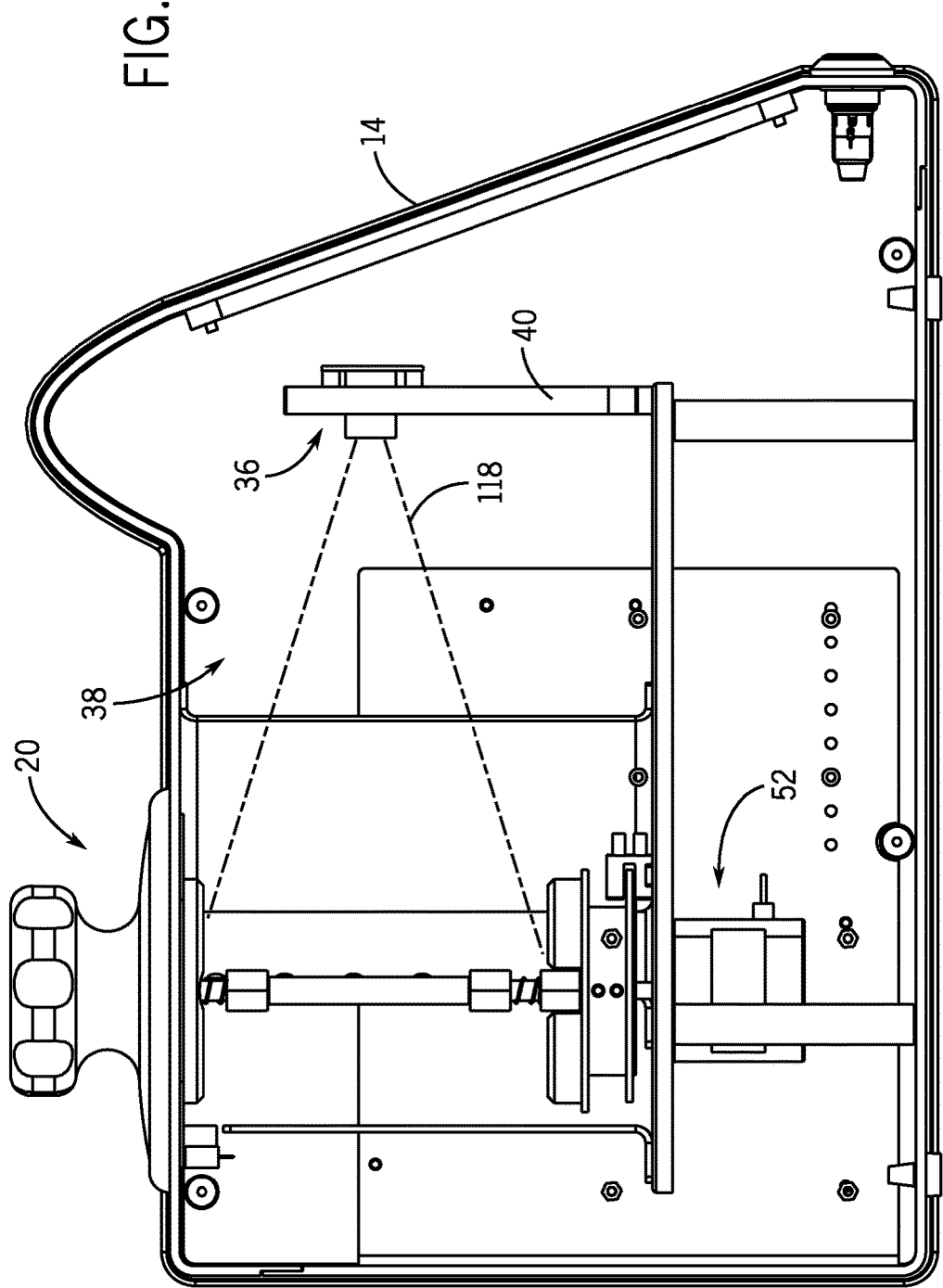
FIG. 9 is a side view of the vision system.
Figure 10:
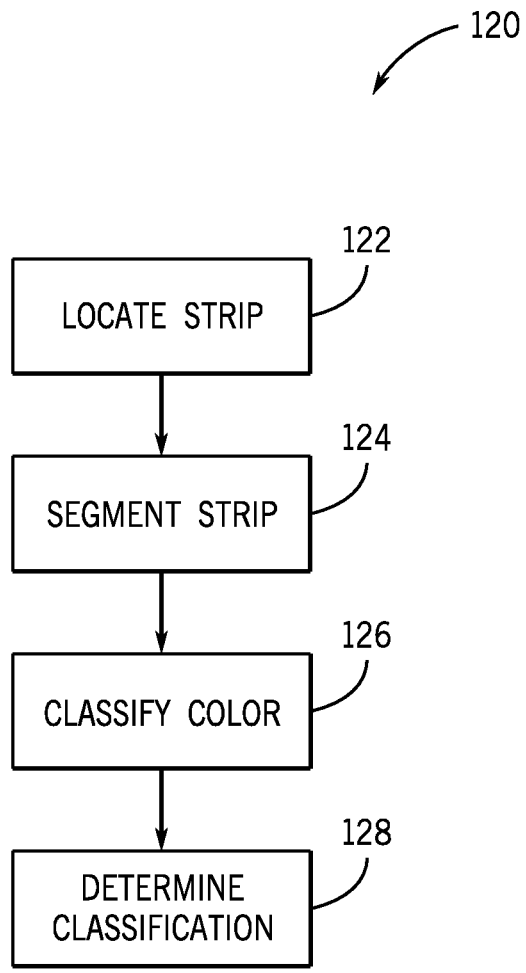
FIG. 10 is a flow diagram of the vision system process.

Referring to FIG. 9 an image chamber includes a color camera 36 that includes a lens that faces the image display. Camera 36 is located a wall 60 of inner housing that is separate from display 14. As will be described below copper strip holder 20 rotates at least 180 degrees so that camera 36 may capture a color image of a first side of the copper strip being analyzed and the second opposing side of the copper strip.

In one embodiment an inner chamber 38 is a separate structure that is removably supported by housing 12. In one embodiment inner chamber 38 is operatively secured to housing 12 and is not removable Referring to FIG. 3 and FIG. 9 inner chamber 38 includes a base 42 supported by a legs 44. Base 42 extends above a bottom 46 of housing 12. A pair of walls 48 extend from base 42 and create a photo chamber region. A back wall 50 is operatively connected to and/or extends from walls 48 to surround test strip holder 20 when the test strip holder is in the operative loaded position. Walls 48 and back wall 50 may have a color and texture such that the optical image of the copper test strip obtained by camera 36 is optimized.

A light or plurality of lights are positioned within housing 12 such that the image chamber is properly illuminated so that camera 36 captures an image of the copper strip relatively free of shadows. The lights may be positioned proximate such that light from the lights are reflected off of walls 48 to provide appropriate lighting of the side of the copper strip facing camera 36.

A drive mechanism 52 located intermediate base 42 of image chamber 38 and bottom 46 of housing 12 is operatively connected to copper strip holder 20 to rotate the copper strip 180 degrees relative to camera 36. In this manner an image of each side of the copper strip is captured and may be stored in memory for processing or processed without being stored in memory. Each side is defined by the surface area that is greater than the edges that define the strip. Referring to FIG. 6 a first side 54 is illustrated having a periphery 56 with a first edge 58 and a second edge 62 separated from and generally parallel to the first edge 58 and a top edge 64 and a bottom edge 66 separated from and generally parallel to one another. Top edge 64 and bottom edge 66 are perpendicular to first edge 58 and second edge 62.

Referring to FIG. 7 test strip holder 20 includes a top handle 68 having a knob 70 and a base member 72. A bushing 74 allows is positioned adjacent a bottom surface of base member 72. A pin 76 operatively couples upper support member 76 to top handle 68. Support member 76 is rotatably coupled to top handle 68. A biasing member 78 is positioned between upper support member 76 and upper holder 80. In one embodiment biasing member 78 is a spring or a pair of springs. However other type of biasing members as are known/in the art are also contemplated.

Upper support member 76 has a pair of apertures 82 that operatively receive an upper end extension 86 of guide posts 84. Upper holder 80 includes a pair of apertures 88 through which upper end 86 of guide posts 84 extend through. Apertures 82 and 88 may include a counter bore to receive an end of biasing member 78 without allowing the end of biasing member 78 to extend fully through apertures 82 and 88. Helical springs 78 act to bias upper holder 80 away from upper support member 76. Upper holder 80 includes an arcuate cut out 90 that faces away from upper support member 76.

Each guide post 84 includes a lower end extension 92. A center portion 94 of guide posts 84 are intermediate lower end extension 92 and upper end extension 86. Center portion 94 has a diameter that is greater than the diameter of lower end extension and the diameter of upper end extension 86. Lower end extension 92 extends through an aperture 96 of lower holder 98. Lower holder 98 includes an arcuate cut out 100 having a groove 102 extending therein to receive bottom edge 66 of test strip 26. The upper edge 64 of test strip 26 is received in a groove having a mirror image to groove 102 in upper holder 80.

A biasing member 104 is positioned between a lower holder 98 and bottom member 106. Lower extension members 92 of guide posts 84 extend through an aperture 108 in lower support 98 and are received within apertures 110 in bottom member 106. Biasing members 78 and 194 are positioned about upper end extension 86 and lower end extension 92 respectively. Biasing member 104 bias lower holder 98 away from bottom member 106 in a direction toward upper member 76. In one embodiment biasing member 104 is a pair of helical springs, however other biasing members known in the art are also contemplated.

Figure 8:
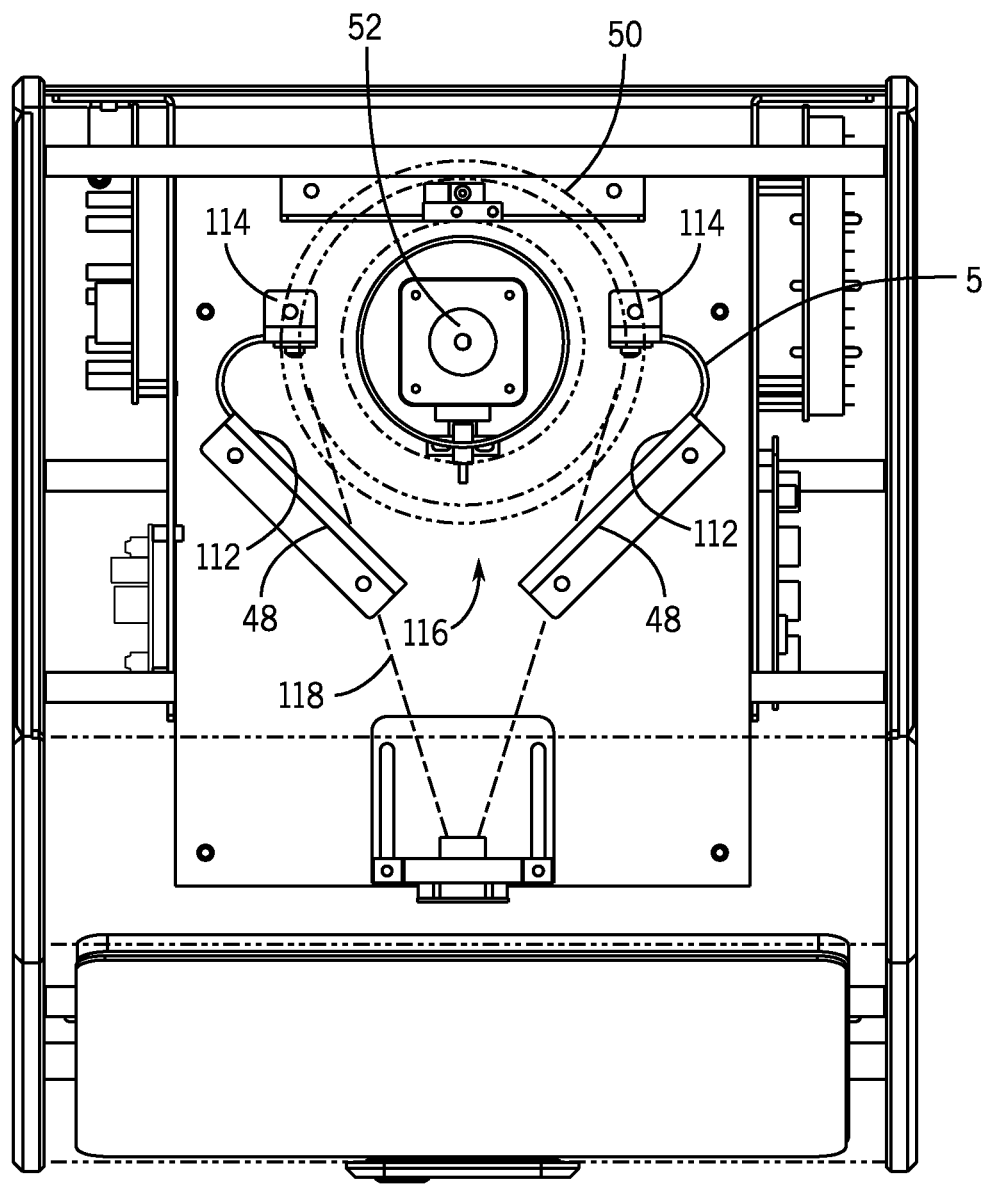
FIG. 8 is a top view of the vision system.

Referring to FIG. 8 walls 48 and back wall 50 define the image region that surround test strip holder 20 when test strip holder is in the loaded position within housing 12. An arcuate wall portion 110 extends from each wall 48. Lights 114 may be positioned on a member proximate an end of arcuate wall portion 110 distal from wall 48. Lights may be reflected of an inner surface 112 of wall 48 to illuminate test strip 26.

Camera 36 has a field of vision 118 that extends through an opening 116 defined by the opening between walls 48 distal to arcuate wall portion 110. Camera 36 is a color digital camera that is operatively connected to a processing unit. Walls 48 include a first rearward edge adjacent arcuate wall portion 110 and a frontward edge closer to camera 36 than the rearward edge. The distance between eh rearward edge of the two walls 48 is greater than the distance between the frontward edge of the two walls. This angled positioning of walls 48 aid in the creation of an image chamber that provides for enhanced illumination of test strip 26 in the loaded position.

For purposes of this application, the term "processing unit" shall mean a presently developed or future developed processing unit that executes sequences of instructions contained in a memory. In one example the term "memory" as used herein comprises a non-transient computer-readable medium containing computer code for the direction of controller. Execution of the sequences of instructions causes the processing unit comprising controller to perform steps such as instructing the digital camera to capture an image of test strip 26 and to process and/or store the signals received from the digital camera. The instructions may be loaded in a random access memory (RAM) for execution by the processing unit from a read only memory (ROM), a mass storage device, or some other persistent storage. In other embodiments, hard wired circuitry may be used in place of or in combination with software instructions to implement the functions described. For example, the processing unit may be embodied as part of one or more application-specific integrated circuits (ASICs). Unless otherwise specifically noted, the processing unit is not limited to any specific combination of hardware circuitry and software, nor to any particular source for the instructions to be executed.

According to one embodiment, a processing unit is stored on a circuit board within housing 12 following instructions contained in memory also stored within housing 12 receives the signals from the digital camera 36 and analyzes such signals, wherein the results of such analysis are presented on display 14.

In operation after a user or lab technician treats a test strip such as a copper test strip by coating the material or dipping the test strip within a product to be tested and processed pursuant to ASTM D130 instructions, a user secures treated test strip to test strip holder 20. Test strip holder 20 is removed from housing 12 by a user gripping knob 70 of top handle 68 and twisting test strip holder 20 about its longitudinal axis to release any lock mechanism between portion 72 and housing 12. A user manually moves upper holder 80 apart from lower holder 98 and places upper edge 64 and lower edge 66 of test strip 26 within grooves 102 of upper edge 64 and lower edge 66 respectively. Biasing elements 78 and 104 act to maintain test strip 26 within test strip holder 20 when the user releases the force to move upper and lower holders apart from one another. Biasing elements 78 and 104 act to move upper and lower holders toward one another thereby securing test strip 26 within test strip holder 20.

Once test strip 26 is securely positioned between upper holder 80 and lower holder 98 the user lowers test strip holder 20 into the housing 12 through the opening 34 in housing 12. Test strip holder 20 is positioned within housing 12 such that base member 72 of handle 68 abuts an upper portion of housing 12. Base member 72 may be operatively locked to upper portion of housing 12 to ensure a secure fit to prevent light from entering the interior of housing 12.

Bottom member 106 is operatively connected to the drive mechanism 52 such that test strip holder 20 may be rotated 180 degrees to present each of the first side of test strip 26 and second side of test strip 26 toward camera 36. Once test strip holder 20 is properly engaged within housing 12 and operatively secured to drive mechanism 52 a user may initiate the analysis of the test strip 26 through a user interface such as a manual switch, a key board, touch screen on display 14, mouse or other user interface. Referring to FIG. 1, a user is prompted to input through the user interface the sample identification so the sample can be tracked. Other information may also be required such as the operator preforming the test, the test method being utilized (e.g. ASTM D130) and a description.

Once the proper tracking data has been entered, a user initiates the analysis of test strip 26 by selecting a graphical user interface or mechanical button. The processor than using instructions from memory initiates the analysis by first causing camera 36 to obtain a digital image of the first side of test strip 26. The digital image of the first side of test strip 26 is then stored in memory. The processor than using instructions from memory causes the drive mechanism to rotate test strip holder 180 degrees to present the second side of test strip 26 toward camera 36. The processor than using instructions from memory initiates the analysis by first causing camera 36 to obtain a digital image of the second side of test strip 26. The digital image of the first side of test strip 26 is then stored in memory. Lights are provided within the interior of housing 12 to properly illuminate the first side and the second side of the test strip 26 as the digital image is being obtained.

In one embodiment camera 36 automatically captures the image of the test strip once the copper strip holder is fully seated into the image chamber. A sensor may trigger the lights in the image chamber to illuminate and the camera may then capture a first image of a first side of the copper test strip and then the motor may rotate the copper strip holder or various aspects of the copper strip holder such that the second side of the copper strip is facing the camera 36. Once the second side of the copper strip is facing camera 56 an image of the second side of the copper strip is captured and forwarded to the processor through which a probability that the color of the copper strip matches the color chart illustrated for example in FIG. 2.

A non-transient computer-readable medium contains computer readable code to direct one or more processing units to analyze the digital images of the first side and the second side of copper strip. The width and height dimensions of the strip are determined from the digital image of the test strip. If the dimensions fall within the acceptable range of the test method or standard selected the processor causes the display to provide an indication that the test strip has passed. Referring to FIG. 1, the size of the test strip is displayed along with an indication if the size passes or fails the test standard.

In one embodiment once test strip 26 is positioned within test strip holder 26 and positioned into housing 12 and operatively engaged with drive mechanism 52 the camera provides a first image of test strip to the processor. In one step the processor through instructions provided in memory identifies the height and width dimensions of test strip 26. The height being the distance between upper edge and lower edge along a vector that extends through and is perpendicular to the upper edge and lower edge. The width being the distance between first edge and second edge taken along a vector that extends through and is perpendicular to the first edge and second edge.

The processor determines if the width and height of the test strip fall between allowable parameters for the test. If the height and or width of the test strip is less than or greater than the permitted range a message is sent to display 14 indicating that the strip size is not in conformance with test requirements. For example if the test requirement is that the height of the test strip is 75 mm+/−5 mm, the minimum height must be greater than 65 mm and less than 80 mm for the test strip to pass.

Once the size of the test strip 26 has been determined from the digital images of the test strip 26, an analysis region is defined that includes an area less than the total area of the test strip 26. The analysis region is selected to avoid analyzing the periphery of the test strip where error may be introduced from shadows that may appear on the outermost periphery of the test strip and any rounding of the test strip as the flat first side and second side transition to the edges. The digital image the first side or side 1 of the test strip 26 and the second side or side 2 of the test strip may be caused to be displayed on display 14 by the processor. In one embodiment the periphery of the region of the test strip being analyzed may be superimposed onto an image of one or both sides of test strip on display 14. In one example the outer periphery of a rectangle may be shown as a dark line on the display of the digital image of the first and/or second side of the test strip on display 14.

The region of the test strip being analyzed is less that the actual surface area of the test strip 26. The region will be located a set distance from the upper edge, lower edge, first side edge and second edge. This avoids any unwanted shadows and/or round edges of the test strip. In one embodiment the region to be analyzed is smaller than the total region by the distance defined by approximately 5-20 pixels. The distance from the edges of the test strip to be excluded from analysis may be adjusted by a user through a user input. As noted above, a rectangle may be displayed in display 14 overlaying the image of the test strip to illustrate the region of analysis.

In one embodiment, the processor divides each image of the first and second sides of the copper strip into a plurality of regions. The color of each region is identified and compared to the ASTM D130 chart. Since the ASTM D130 chart includes certain categories that include more than one color an algorithm is used to compare the plurality of regions to the colors in each of the categories of the ASTM chart. A probability or rating is assigned to each captured digital image that it falls within a particular category of the ASTM chart. The results may be stored in memory for later use and/or may be displayed on the display. By way of example and referring to FIG. 2 a strip test that has multiple colors may have a first probability that the colors of the copper strip matches the colors in category 2c and may be assigned a second probability that the colors of the copper strip match the colors in category 3b.

A user may review the relative probabilities and add his/her comments as to their conclusion through the user input device and/or touch screen. The algorithm used to determine the probability that the color(s) of the copper test strip may also take into account the change of colors from region to region to match the type of curved/arcuate color sections in the various categories.

In addition to the height and width of test strip the location of the region of the test strip to be evaluated is also determined. The determination of the color of the test strip is determined by regions of the test strip which are identified by location from the edges.

An image of the first side of the test strip 26 is obtained by camera 36 and stored in memory. Processor processes the digital data by segmenting the entire data into small sections or regions. In one embodiment each section includes a square area defined by a 4 by 4 pixel area for a total of 16 pixels. Each of the 16 pixel sections are analyzed in a classifier module. In one embodiment the total number of sections is 30,000 per strip. The number of sections will depend on the number of pixels available for analysis with the digital camera being used.

The digital camera 36 provides information related to the hue, value or tone, and intensity or chromatic intensity for each pixel. The 16 data from the sixteen pixels are analyzed in an algorithm that utilizes the data from all 16 pixels and provides a single color value and then categorized by the classifier module. In one embodiment each pixel is analyzed by itself. In one embodiment the segmented area or region includes more than 16 pixels. The classifier module utilizes an algorithm to identify which of the discrete number of categories of colors the region falls within. Referring to ASTM standard D130 the number of colors in each of the categories may be reduced to a discrete number of colors such as 12. A number of the ASTM categories have a single color, while a number of the ASTM categories include more than one color. For example categories 2c, 3a, and 3b include more than one color. Accordingly, a section of pixels falling into one color category may be found in more than one category of the ASTM D130 standard.

In one embodiment the colors included in each category are identified and define color categories. Each color category may include a range of color as a function of hue, value and intensity. The color of each pixel is identified. If the color falls within the range identified with each color category then that pixel section is assigned the particular color category value. The results are then accumulated and the sum of all of the sections that fall within each color category is aggregated. The determination as to the likelihood that the colors identified in each test strip sample falls within which ASTM D130 category is discussed below.

Once all of the sections have been analyzed and the particular category identified the processor determines the percentage of each color identified. Additionally, the processor utilizing an algorithm to identify the likelihood that one of the categories on the ASTM standard that includes multiple colors is the correct match for the test strip.

Given a set of training examples, each marked as belonging to one of two categories, an Support Vector Machine (SVM) training algorithm builds a model that assigns new examples into one category or the other. The SVM algorithm may create the color range for each category of the ASTM standard by referencing a plurality of digital test strips having various colors that all fall within a given category.

The appropriate range of colors that distinguish one category for another is then created and used for comparison purposes for an actual test strip. It is possible to provide separate libraries for different types of fluids being analyzed. Where a particular fluid provide different colors on the copper test strips than other fluids a separate library of colors are used for a given fluid type. Similarly, if copper test strips from different batches of test strips have different material compositions a library may be accessed for the particular batch of test strips. In this manner system 10 allows for the creation of a portable Color Model Library (saved in xml), to allow for different color libraries to be used in different environments.

Solid color ratings (e.g. 1a of ASTM standard D130) are determined by comparing pixel data against stored colors. Ratings that contain multiple colors are determined by identifying a collection of identified colors. For example, in order for a rating 2c of ASTM standard D130, the sample must contain a combination of Slight Tarnish, Corrosion, and a Red colored Moderate Tarnish. The logic is described below.

Now turning to the method in which a determination is made as to which category of the ASTM standard best fits the test sample. In one embodiment a total of 13 color ranges are identified that correlate to the 13 different color ranges found in the categories in the ASTM standard. It is contemplated that fewer or more than 13 different color ranges may be used with this system. It is noted that some categories include more than one color range. For each section of the test strip sampled a count is created if the pixel region is correlated to a given color range. Once all of the pixels and/or pixel regions have been identified within a given color range and counted. For example if 30 pixels or pixel regions are associated with color range 1, the count for color range 1 would be 30. The next step is to associate the count with the ASTM standards. Where an ASTM standard includes a single color range the count for the ASTM category would be the same as the count for the color range. For example if 30 pixel regions were associated with color range 1 and color range 1 is the only color in ASTM D130 category 1a, then category 1a would also have a count of 30. Where a category such as 2c that includes various color ranges an algorithm is used to determine whether there is sufficient basis to provide a count for the categories having more than one color range.

To determine the count for category 2c the number of percentage of the total number of sections must have at least 10% Corrosion and 10% Slight Tarnish or 10% Moderate Tarnish Red color categories. The following algorithm may be used: If (4a+4b+4c)>10% And ((1a+1b)>10% Or (2a+2b)>10%) Then 2c Count=(4a+4b+4c)+(1a+1b)+(2a+2b). Similarly, for the count of category 3a the percentage of the percentage of the number of sections must have 10% Moderate Tan and 10% Moderate Tarnish Red. The following algorithm may be used: If (2d+2e)>10% And (2a+2b)>10%) Then 3a Count=(2d+2e)+(2a+2b).

To determine the count for category 3b the number of percentage of the total number of sections must have at least 10% trained Color 3b Green. The following algorithm may be used: If (3bGreen)>10% then 3b Count=(1a+1b)+(2d+2e)+(3bGreen)+(4a+4b+4c).

Note that a threshold of 10% is used to determine whether there is sufficient basis to assign a count to the ASTM category with more than one color range. The parentage factor is the percentage of combination of colors as a percent of the total count for all color categories. By way of a simple example if the count for a category X having two colors 1a and 1b, we provide a count to X=the count of 1a+the count of 1b only if the sum of count 1a and 1b is greater than 10% of the total count. So in one example the total count of pixel regions evaluated that fall within the color 1a is 50 and the total count of pixel regions evaluated fall within the color 1b is 70, where the total count of all of the pixel regions evaluated is 1000. In this example the sum of the count of 1a and the count of 1b is 50+70=120. So the count of 120 would be applied to category X if the sum of 1a and 1b is greater than 10% of the total count which in this example is 1000. Since 120 is 12% of 1000, the test is passed and a count of 120 is provided to category X. The percentage used to set the threshold of determining whether to apply a count to a category with more than one color may be modified by a user and or adjusted.

Copper corrosivity is an indicator of sulfur compounds present after the refining process. Measuring corrosivity continues to be a challenge, as no accurate standardized test has been developed to date. Manual; corrosivity tests involve manual and visual assessments, which can introduce human error and bias. The Copper Digital Detection Imaging (CuDDI) system described herein provides a repeatable analysis regarding the level of corrosivity present from petroleum. In one embodiment through a four-step automated vision algorithm and classification process, results are digitally recorded and are seamlessly integrated with LIMS software.

The vision system 10 includes a vision algorithm and vision system records, calculates and displays accurate corrosivity ratings in a short period of time in a few seconds. A high-resolution digital camera provides high resolution image of the copper strips being analyzed and a drive system 52 provides for accurate rotation of the copper test strip.

The CuDDI method includes inserting the test strip into a test strip holder and loading the test strip and test strip holder into the housing 12. An LED light source is automatically activated and regulated to illuminate the test strip. Software instructions in memory provide instructions to a processor to identify and capture a first image of a first side of the test strip. The processor using software instructions in memory then causes the drive mechanism to rotate the test strip holder 180 degrees and capture a second image of the second side of the test strip. The analyses of the color digital images are processed and through a CuDDI algorithm. Final results are displayed on a high-resolution touch screen display 14.

The apparatus and method described herein to evaluate the corrosiveness of the copper test strips allow for digital imaging, storage of the test results for future analysis and record keeping and repeatable calculation of results. The system may be connected to an internet network with direct LIMS Connectivity utilizing a USB, Ethernet and HDMI Outputs. The system removes worker bias and eliminates a manual rating assessment. The lighting is voltage and electric current controlled to provide consistent ambient light environment for assessment of the test strips. The system provides for accurate and automatic detection of copper strip size to ensure that the test strip meets industry ASTM standards. Both sides of the test strip are evaluated and taken into account when providing the final assessment of likelihood of categorization within the ASTM standard. The test strip holder provides for single hand loading reducing the likelihood of user fingerprints and/or unwanted markings on the test strips. The system identifies and records a first side and second side for analysis and record keeping.

In one embodiment the system provides analysis for ASTM D130 and D1838 and analyzing categories 1a to 4C provided therein. The color is detected using digital video detection using a CMOS detector. In one embodiment the light source is proximately LED 7,000K. The measuring and analysis time is under 30 seconds.

The device 10 may be calibrated utilizing standard test strips of known type copper thickness and color correlating to the ASTM standard categories 1a, 1b, 2a, 2b, 2c, 2e, 3a, 3b, 4a, 4b, and 4c. Or other categories in an ASTM or other standard.

Referring to FIG. 1a and FIG. 1b each side of the test strip may be displayed on display 14 along with the rank scores showing the likelihood that the test strip falls within a given category of ASTM standard D130. While on FIG. 1 both sides are shown with the single most likely determination of the proper classification for the test strip as a whole including the results from the first side and second side of the test strip. In one embodiment the color associated with a region of the test strip can be displayed by a user hovering a user interface over the region of interest.

While the foregoing written description of the invention enables one of ordinary skill to make and use what is considered presently to be the best mode thereof, those of ordinary skill will understand and appreciate the existence of variations, combinations, and equivalents of the specific embodiment, method, and examples herein. The invention should therefore not be limited by the above described embodiment, method, and examples, but by all embodiments and methods within the scope and spirit of the invention.

What is claimed is:

1. An apparatus for analyzing the color of a test strip:
   a housing operatively supporting a vision system;
   a test strip holder configured to support a test strip;
   a drive mechanism operatively coupled to the test strip holder to rotate the test strip holder 180 degrees; and
   a processing unit operatively coupled to the vision system to receive digital image data of a first side of the test strip and a second side of the test strip;
   the processing unit including instructions to analyze the received imaging data; and compare the imaging data to a known standard having a plurality of categories, wherein each category includes at least one color range, and at least one of the plurality of categories includes more than one color range;
   wherein the imaging data includes a plurality of pixels, the processing unit identifying the color range of each of the plurality of pixels and determining a number of pixels falling within each color range;
   the processing unit determining a count for each category based upon at least a threshold percentage of a sum of the pixels falling within each of the color ranges of the category of all the pixels;
   the processing unit identifying the likelihood that the test strip is covered by each of the categories based upon the count for each category;
   wherein the processing unit includes instructions to segment the digital image into a plurality of regions having a plurality of pixels and determine the color range of each region;
   wherein the processing unit includes a classifier module including instructions to compare each color range of each of the plurality of regions to a discrete number of categories wherein the discrete number of categories is greater than one; and
   wherein determining the likelihood that the test strip is covered by one of the categories includes utilizing a threshold percentage of the combination of colors of the total number of regions evaluated.

2. The apparatus of claim 1, wherein the known color of the test strip is an indication of corrosiveness.

3. The apparatus of claim 1, wherein the vision system includes a digital color camera.

4. The apparatus of claim 3, including a first wall and a second defining an opening there between defining a field of vision for the camera.

5. The apparatus of claim 4, including at least one light source shining off at least one of the first wall and second wall to illuminate the test strip.

6. The apparatus of claim 1, wherein the test strip holder is removably received within the housing.

7. The apparatus of claim 6, wherein the test strip holder has a self-centering portion to center a test strip between an upper region and a lower region of the test strip holder.

8. The apparatus of claim 7, wherein the test strip holder has a biasing element to bias the test strip to a center position between the upper region and the lower region.

9. The apparatus of claim 6, wherein the test strip holder is operatively received through an aperture in the housing.

10. The apparatus of claim 1, wherein the processing unit is configured to display the test strip and results of the analysis on a display.

11. The apparatus of claim 3, wherein the camera automatically obtains a first image from a first side of a test strip and a second image from an opposing second side of the test strip after the drive mechanism rotates the test strip holder from a first position to a second position 180 degrees from the first position.

12. An apparatus for analyzing the color of a test strip:
a housing operatively supporting a vision system;
a test strip holder configured to support a test strip;
a drive mechanism operatively coupled to the test strip holder to rotate the test strip holder 180 degrees; and
a processing unit operatively coupled to the vision system to receive digital image data of a first side of the test strip and a second side of the test strip;
the processing unit including instructions to analyze the received imaging data; and compare the imaging data to a known standard having a plurality of categories, wherein each category includes at least one color range, and at least one of the plurality of categories includes more than one color range;
wherein the imaging data includes a plurality of pixels, the processing unit identifying the color range of each of the plurality of pixels and determining a number of pixels falling within each color range;
the processing unit determining a count for each category based upon at least a threshold percentage of a sum of the pixels falling within each of the color ranges of the category of all the pixels;
the processing unit identifying the likelihood that the test strip is covered by each of the categories based upon the count for each category;
wherein the processing unit includes instructions to segment the digital image into a plurality of regions having a plurality of pixels and determine the color range of each region;
wherein the processing unit includes a classifier module including instructions to compare each color range of each of the plurality of regions to a discrete number of categories wherein the discrete number of categories is greater than one; and
wherein each region has 16 or more pixels.

13. An apparatus for analyzing the color of a test strip:
a housing operatively supporting a vision system,
a test strip holder configured to support a test strip, wherein the test strip holder is operatively locked to an upper portion of the housing to ensure a secure fit to prevent light from entering an interior of housing;
a light source being positioned within the housing such that the light source illuminates the test strip by light reflected from an inner wall;
a drive mechanism operatively coupled to the test strip holder to rotate the test strip holder 180 degrees; and
a processing unit operatively coupled to the vision system to receive digital image data of a first side of the test strip and a second side of the test strip;
the processing unit including instructions to analyze the received imaging data; and compare the imaging data to a known standard having a plurality of categories, wherein each category includes at least one color range, and at least one of the plurality of categories includes more than one color range.

* * * * *